United States Patent [19]

Eicken et al.

[11] 4,336,061
[45] Jun. 22, 1982

[54] HERBICIDAL AZOLYL CHLOROACETANILIDES, COMPOSITIONS AND METHOD OF USE

[75] Inventors: Karl Eicken, Wachenheim; Wolfgang Rohr, Mannheim; Norbert Goetz, Worms; Bruno Wuerzer, Limburgerhof, all of Fed. Rep. of Germany

[73] Assignee: BASF Aktiengesellschaft, Fed. Rep. of Germany

[21] Appl. No.: 196,734

[22] PCT Filed: Apr. 10, 1979

[86] PCT No.: PCT/EP79/00076

§ 371 Date: Sep. 6, 1980

§ 102(e) Date: May 6, 1980

[87] PCT Pub. No.: WO80/00701

PCT Pub. Date: Apr. 17, 1980

[30] Foreign Application Priority Data

Oct. 7, 1978 [DE] Fed. Rep. of Germany ....... 2843869

[51] Int. Cl.³ .................... A01N 43/50; A01N 43/56; A01N 43/64; C07D 231/12; C07D 233/61; C07D 249/04; C07D 249/08

[52] U.S. Cl. ........................................ 71/92; 548/375; 548/376; 548/378; 548/255; 548/262; 548/264; 548/265; 548/337; 548/341

[58] Field of Search ............... 548/375, 376, 378, 255, 548/262, 264, 265, 337, 341; 71/92

[56] References Cited

U.S. PATENT DOCUMENTS 3,547,620 12/1970 Olin ....................................... 71/118

FOREIGN PATENT DOCUMENTS 2328340 12/1973 Fed. Rep. of Germany .
2648008 5/1978 Fed. Rep. of Germany .
2379525 9/1978 France .

Primary Examiner—Henry R. Jiles
Assistant Examiner—N. Harkaway
Attorney, Agent, or Firm—Keil & Witherspoon

[57] ABSTRACT

The present invention relates to acetanilides, processes for the manufacture of these acetanilides, herbicides containing these compounds, and processes for combating the growth of unwanted plants with these compounds.

6 Claims, No Drawings

HERBICIDAL AZOLYL CHLOROACETANILIDES, COMPOSITIONS AND METHOD OF USE

FIELD OF THE INVENTION

The invention is used for combating unwanted plants.

Characteristics of prior art technical solutions

Haloacetanilides which have herbicidal or growth-regulating properties have been disclosed. The compound 2-chloro-2',6'-diethyl-N-methoxymethylacetanilide (U.S. Pat. No. 3,547,620) has achieved considerable economic importance. A further active ingredient which has been disclosed is 2-chloro-2'-ethyl-6'-methyl-N-(1'-methoxyprop-2'-yl)-acetanilide (German Published Application DE-AS No. 2,328,340). This compound exhibits, in addition to a good action on unwanted grasses, good persistence in the soil.

Object of the invention

The object of the invention is to develop herbicidal agents having increased activity.

Description of the essence of the invention

The invention is based on the desire to provide a new herbicidal agent.

It has been found that a herbicide containing an acetanilide of the formula

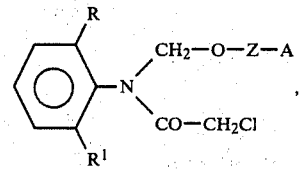

where R and R$^1$ are identical or different and each denotes alkyl of 1 to 4 carbon atoms, Z denotes methylene, or ethylene which is unsubstituted or substituted by 1 or 2 methyl groups, and A denotes pyrazole which is linked via a ring nitrogen atom and is unsubstituted or mono- or disubstituted by halogen, methyl or methoxy, triazole which is linked via a ring nitrogen atom and is unsubstituted or mono- or disubstituted by halogen, methyl or methoxy, or imidazole which is linked via a ring nitrogen atom and is unsubstituted or mono- or disubstituted by halogen, methyl or methoxy, has a broadened herbicidal action and is well tolerated by important crop plants.

Depending on the aim to be achieved and the application rate, the new active ingredients are suitable for the selective control of unwanted plants in certain crops consisting of herbaceous or woody plant species, for growth regulation by inhibiting plant growth, or, at appropriately high application rates, for total elimination of plant growth.

The following are suitable meanings for R, R$^1$, Z and A:

R and R$^1$ denote alkyl of 1 to 4 carbon atoms, such as methyl, ethyl, n-propyl, isopropyl, n-butyl, sec-butyl, and tert-butyl;

Z denotes methylene, or ethylene which is unsubstituted or substituted by 1 or 2 methyl groups, such as ethylene (—CH$_2$—CH$_2$—), 1-methylethylene, 2-methylethylene, and 1,2-dimethylethylene;

A denotes pyrazole, triazole or imidazole, each of which is linked via a ring nitrogen atom and is unsubstituted or mono- or disubstituted by halogen, methyl or methoxy, such as 3(5)-methylpyrazole, 4-methylpyrazole, 3,5-dimethylpyrazole, 4-chloropyrazole, 4-bromopyrazole, 4-methoxypyrazole, 3(5)-methyl-5(3)-methoxypyrazole, 4(5)-methyl-1,2,3-triazole, 4,5-dimethyl-1,2,3-triazole, 3(5)-methyl-1,2,4-triazole, 3,5-dimethyl-1,2,4-triazole, 4,5-dichloroimidazole, and 4,5-dibromoimidazole.

In certain asymmetrically substituted azoles, such as pyrazole, 1,2,3-triazole, 1,2,4-triazole and imidazole, two isomers appear in the starting materials because of tautomeric structures, as is illustrated here with reference to pyrazole:

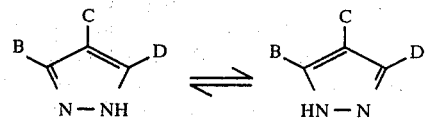

In these instances, therefore, two isomers appear in the new acetanilides; the ratio of the one to the other is determined mainly by the type of the radicals B, C and D and may be of significance for the herbicidal properties.

The new acetanilides may be produced by the following process. They are obtained by reaction of 2-chloro-N-chloromethylacetanilides of the formula II with an alcohol of the formula III in accordance with the following equation:

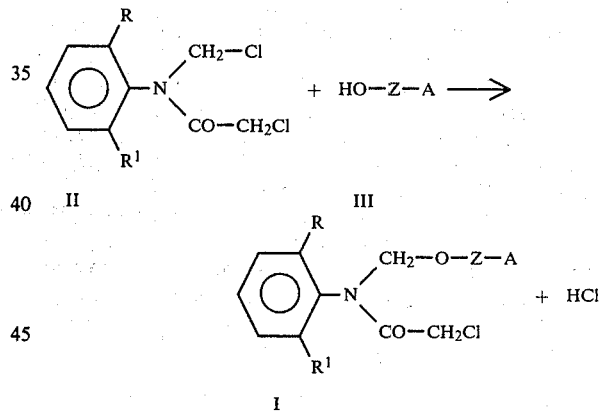

The substituents R, R$^1$, Z and A have the above meanings. Some of the 2-chloro-N-chloromethylacetanilides of the formula II are disclosed in U.S. Pat. No. 3,637,847; others may be produced analogously by reaction of the corresponding azomethines with chloroacetyl chloride.

Advantageously, the alcohol of the formula III is employed in at least the molar amount, with reference to 2-chloro-N-chloromethylacetanilide.

The hydrogen chloride liberated during the reaction may be removed as gas, or intercepted by suitable binders, such as organic bases, e.g., tertiary amines, or inorganic bases, e.g., alkali metal carbonates. The hydrogen chloride binder is used in at least the molar amount, with reference to 2-chloro-N-chloromethylacetanilide employed.

When the 2-chloro-N-chloromethylacetanilides of the formula II are reacted with alcohols of the formula III in which Z is methylene (—CH$_2$—), it is particularly advantageous to use the alcohols in the form of their alkali metal salts. These alkali metal salts may generally be produced by reaction of 1-hydroxymethyl azoles with strong bases, such as organometal compounds, e.g., butyllithium and methylmagnesium chloride; alkali metal hydrides, e.g., sodium hydride; alkali metal amides, sodium amide; and alkali metal alcoholates, e.g., sodium methylate, with the elimination of hydrogen, alkane, ammonia or methanol.

It is advantageous to carry out the reaction in a solvent inert to 2-chloro-N-chloromethylacetanilides. Suitable examples are hydrocarbons, such as toluene and xylene; ethers, such as diethyl ether, tert-butylmethyl ether, 1,2-dimethoxyethane, tetrahydrofuran and dioxane; esters, such as ethyl acetate and butyl acetate; nitriles, such as acetonitrile and propionitrile; sulfones, such as dimethyl sulfoxide and tetrahydrothiophene-1,1-dioxide; and secondary amides, such as N,N-dimethylformamide and N,N-diethylformamide. Mixtures of these solvents may also be used. Particularly when alkali metal salts of the 1-hydroxymethyl azoles of the formula III (Z denoting methylene (—CH$_2$—)) are reacted, it is advantageous to carry out the reaction in aprotic, polar solvents or mixtures with these solvents.

The reaction of the 2-chloro-N-chloromethylacetanilides of the formula II with the alcohols of the formula III, or the alkali metal salts of these alcohols, is carried out at from −30° to ±50° C., preferably at room temperature. The reaction products are—if desired after separation of byproducts which have formed, such as alkali metal chloride or trialkylammonium chlorides, and, if desired, after replacement of the polar aprotic solvent by a water-immiscible solvent—isolated in conventional manner.

Some of the alcohols of the formula III used for the manufacture of the acetanilides of the formula I according to the invention are known, e.g., 1-hydroxymethyl-pyrazoles and 1-(2-hydroxyethyl)-pyrazoles (Chem. Ber., 85, 820, 1952; J. Chem. Soc., 1960, 5272).

A simple method of preparing 1-(2-hydroxyethyl)-azoles and 1-(2-hydroxypropyl)-azoles is to react epoxides with azoles in conventional manner in accordance with the following equation (cf. Manufacturing Example A):

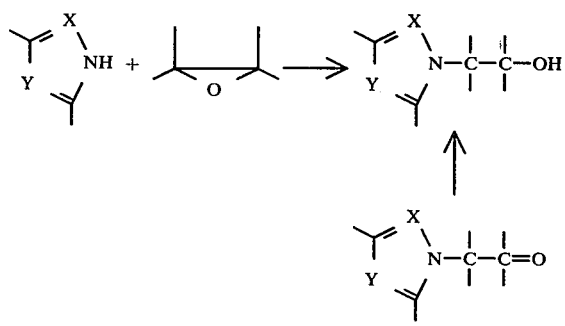

X and Y denote C or N, and at least one of the two atoms X and Y is always N.

These alcohols may also be manufactured by reduction of the corresponding α-azol-1-yl-ketones or -aldehydes with, for example, complex hydrides, such as sodium borohydride, in an alcohol or tetrahydrofuran.

In the following examples, parts by weight bear the same relationship to parts by volume as kilograms to liters.

EXAMPLE A 2 parts by volume of water is added to a solution of 136 parts by weight of pyrazole in 500 parts by weight of 4-methylmorpholine, and the mixture is heated to 140° C. in a stirred autoclave having a capacity of 1,000 parts by volume. Once this temperature has been reached, 100 parts by weight of ethylene oxide is pressured in. The mixture is then allowed to react at 140° C. for 5 hours. The mixture which is obtained is worked up by distillation; there is obtained 195 parts by weight (87% of theory) of 1-(2-hydroxyethyl)-pyrazole, b.p. (0.01 mm): 87° C.

The following alcohols of the formula III may be manufactured analogously:

| Structure | b.p. (mm) | °C |
|---|---|---|
| pyrazole-N—CH$_2$CH(CH$_3$)—OH | b.p. (0.01) | = 66° C. |
| 1,2,4-triazole-N—CH$_2$—CH$_2$OH | b.p. (0.05) | − 129° C. |
| 1,2,4-triazole-N—CH$_2$—CH(CH$_3$)—OH | b.p. (0.05) | = 112° C. |
| pyrazole-N—CH$_2$—CH$_2$OH | b.p. (0.01) | = 146° C. |
| pyrazole-N—CH$_2$—CH(CH$_3$)—OH | b.p. (0.15) | = 143° C. |
| 3,5-dichloropyrazole-N—CH$_2$—CH$_2$OH | b.p. (0.01) | = 148° C. |
| 3,5-dichloropyrazole-N—CH$_2$—CH(CH$_3$)—OH | b.p. (0.01) | = 115° C. |

The following example illustrates the preparation of the new acetanilides.

EXAMPLE 1

At 15° to 20° C., 3.6 parts by weight of sodium hydride is introduced in portions into a solution of 14.7 parts by weight of 1-hydroxymethylpyrazole in 65 parts by volume of anhydrous tetrahydrofuran, and the mixture is stirred until no more hydrogen evolves (2 hours). At −10° C., a solution of 36.9 parts by weight of 2-chloro-2',6'-dimethyl-N-chloromethylacetanilide in 100 parts by volume of anhydrous acetonitrile is dripped into this mixture, and the whole is stirred overnight at room temperature. After the solvents have been evaporated in vacuo, the residue is dissolved in 100 parts by volume of methylene chloride, washed with water, then with 1 N HCl solution, then with saturated bicarbonate solution, and subsequently twice with water, dried over sodium sulfate, and filtered. The filtrate is stirred with 4 parts by weight of silica gel and 2 parts by weight of activated charcoal for 2 hours and, after filtration, concentrated in vacuo at 50° C. After cooling, the residue gives 32.6 parts by weight of 2-chloro-2',6'-dimethyl-N-(pyrazol-1-yl-methylenoxymethyl)-acetanilide, m.p.: 73°-74° C. (active ingredient 1).

| $C_{15}H_{18}ClN_3O_7$ (MW 308) | | | |
|---|---|---|---|
| | C | H | N |
| cal.: | 58.5 | 5.9 | 13.7 |
| found: | 57.7 | 5.8 | 13.7 |

The following compounds are prepared analogously:

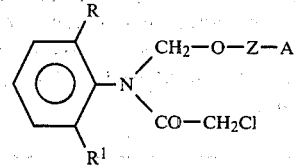

| Compound no. | R | R¹ | Z | A | m.p./$n_D$ |
|---|---|---|---|---|---|
| 2 | CH₃ | C₂H₅ | CH₂ | pyrazolyl | oil |
| 3 | CH₃ | CH₃ | CH₂—CH₂ | pyrazolyl | 64° C. |
| 4 | CH₃ | C₂H₅ | CH₂—CH₂ | pyrazolyl | oil |
| 5 | CH₃ | CH₃ | CH₂—CH₂ | 1,2,4-triazolyl | |
| 6 | CH₃ | CH₃ | CH(CH₃)—CH₂ | 1,2,4-triazolyl | |
| 7 | CH₃ | CH₃ | CH₂—CH₂ | 3,4-dichloropyrazolyl | 78° C. |
| 8 | CH₃ | CH₃ | CH₂ | 3,5-dimethylpyrazolyl | |
| 9 | CH₃ | CH₃ | CH₂ | 4-methylpyrazolyl | |
| 10 | CH₃ | C₂H₅ | CH₂ | 4-methylpyrazolyl | |
| 11 | CH₃ | CH₃ | CH₂ | 4-chloropyrazolyl | |
| 12 | CH₃ | CH₃ | CH(CH₃)—CH₂ | pyrazolyl | oil |
| 13 | CH₃ | C₂H₅ | CH(CH₃)—CH₂ | pyrazolyl | 1.5481 |

The compounds of the invention can be converted into the conventional formulations, e.g. solutions, emulsions, suspensions, dusts, powders, pastes and granules. The form of application depends entirely on the purpose for which the agents are being used; it should, however, ensure a fine and uniform distribution of the active ingredient. The formulations are prepared in the conventional manner, for example by diluting the active ingredient with solvent and/or carriers, with or without the addition of emulsifiers and dispersants and, where water is used as the diluent, with or without organic auxiliary solvents. Suitable auxiliaries are, essentially, solvents for example aromatics, e.g., xylene and benzene, chloroaromatics, e.g. chlorobenzene, paraffins, e.g. petroleum fractions, alcohols, e.g. methanol and butanol, amines, e.g., ethanolamine, dimethylformamide, and water; solid carriers, for example natural rock powders, e.g. kaolin, alumina, talc and chalk, and synthetic rock powders, e.g. highly disperse silica and silicates; emulsifiers, for example non-ionic and anionic emulsifiers, e.g. polyoxyethylene fatty alcohol ethers, alkylsulfonates and arylsulfonates, and dispersants, for example lignin, sulfite waste liquors and methylcellulose.

The agent in general contain from 0.1 to 95% by weight of active ingredient, preferably from 0.5 to 90%.

The agents, and the ready-to-use preparations obtained therefrom, e.g., solutions, emulsions, suspensions, powders, dusts, pastes or granules, are applied in conventional manner, e.g. by spraying, atomizing, dusting, broadcasting, dressing seed, or watering.

The application rates depend on the type of effect desired, and are from 0.1 to 15 and more, but preferably from 0.25 to 3, kg of active ingredient per hectare.

The new herbicidal anilides may be mixed and applied together with numerous representatives of other herbicidal or growth-regulating active ingredient groups. Examples of suitable components for mixtures are diazines, benzothiadiazinones, 2,6-dinitroanilines, N-phenylcarbamates, biscarbamates, thiolcarbamates, halocarboxylic acids, triazines, amides, ureas, diphenyl ethers, triazinones, uracils, benzofuran derivatives, etc.

These combinations broaden the spectrum of action, and in some instances synergistic effects are achieved. A number of active ingredients which, when combined with the new active ingredients, give mixtures suitable for widely varying areas of application are given below by way of example:
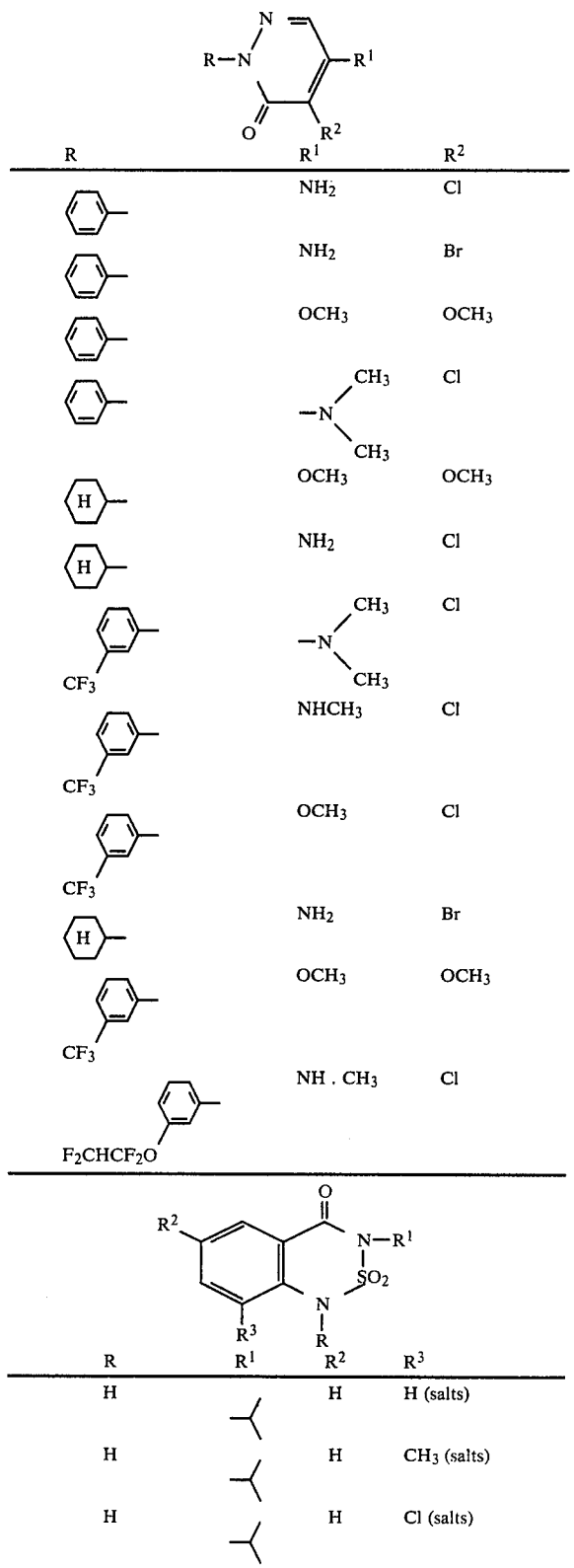
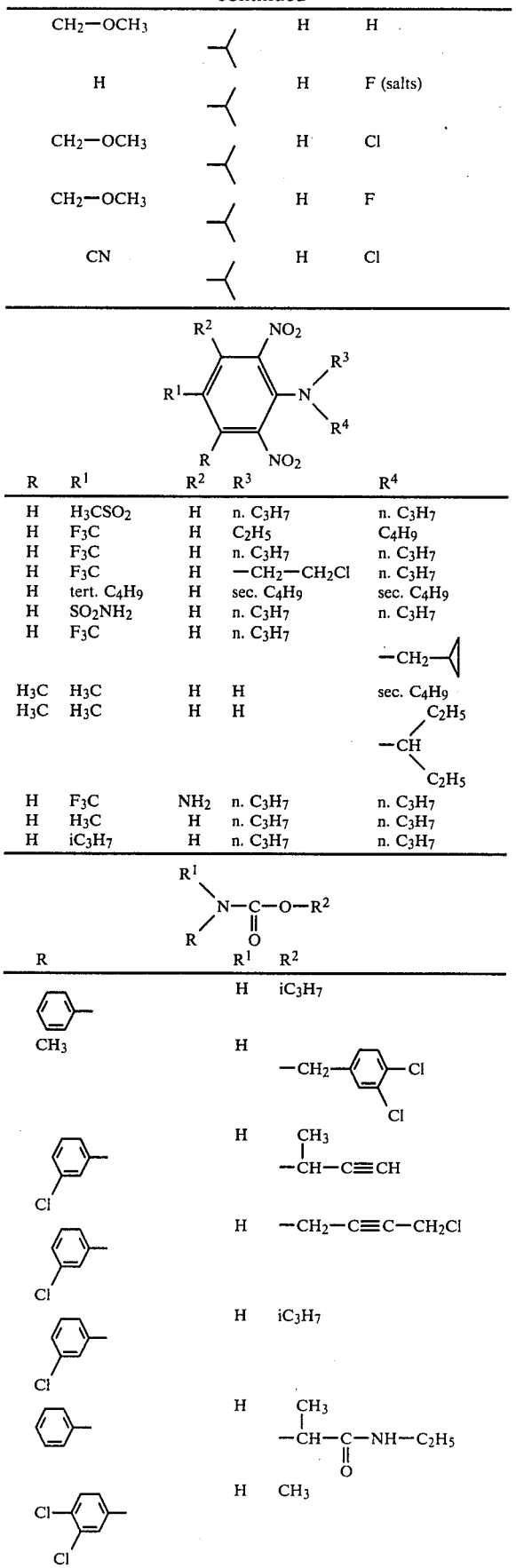

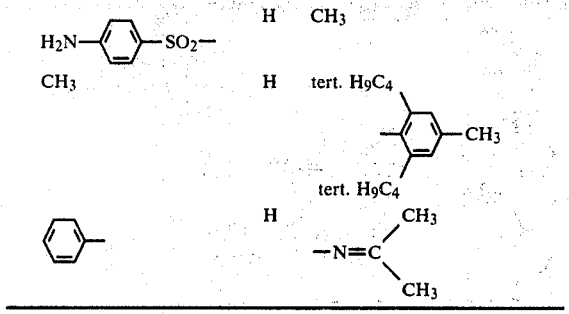
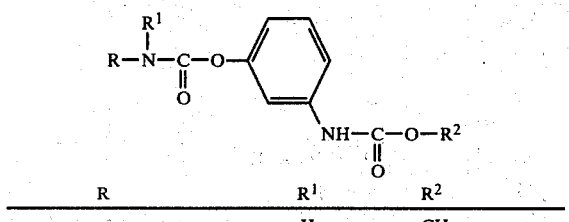
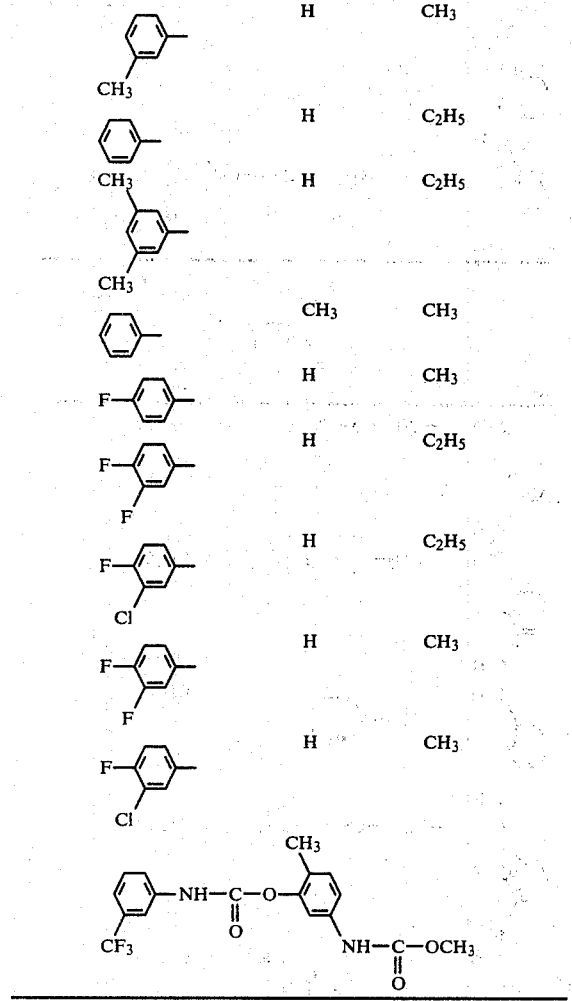
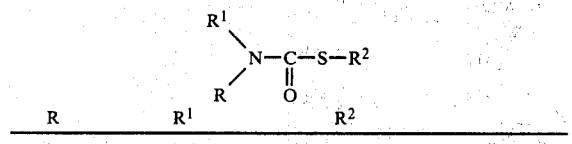
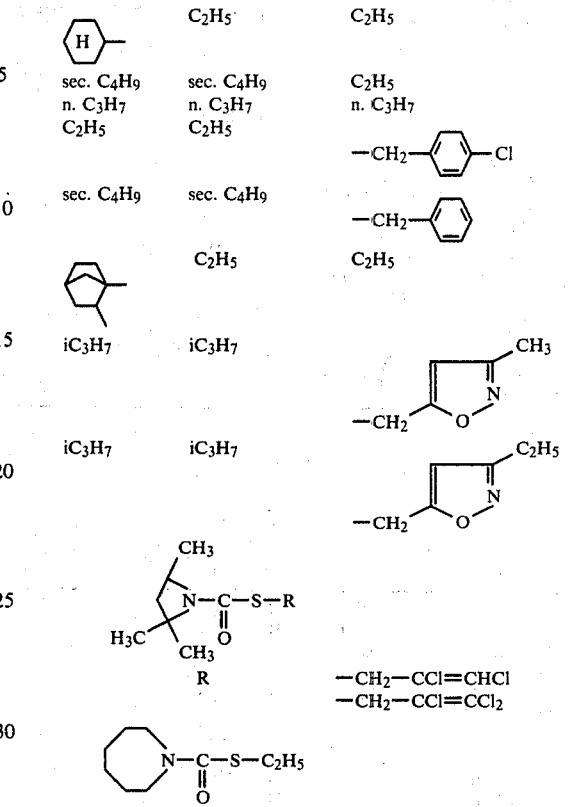
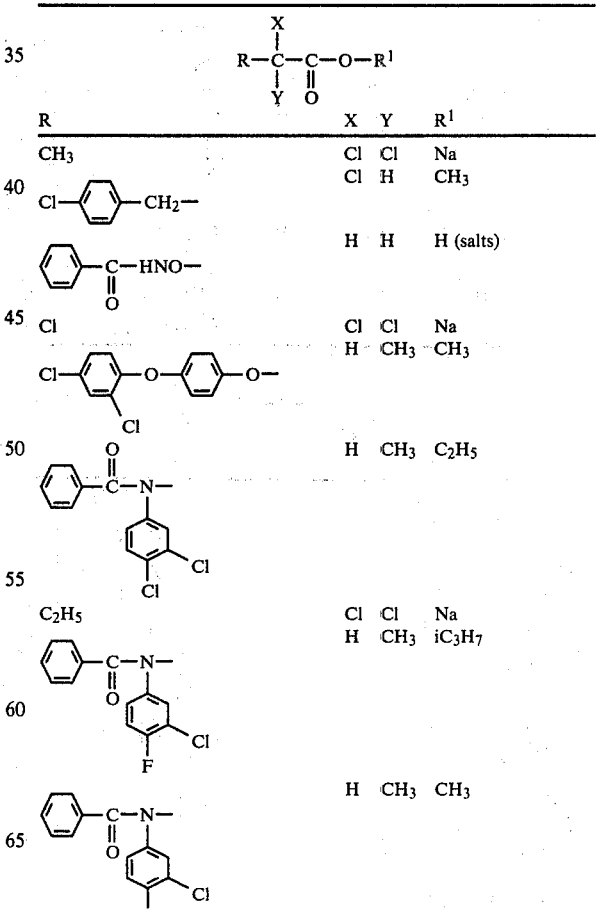

-continued

| Structure | | | |
|---|---|---|---|
| 4-ClC6H4-O-C6H4-O-CH3 | H | CH3 | -CH2-CH(CH3)CH3 |
| 3,5-dichloro-2-(4-methoxyphenoxy)pyridine | H | CH3 | Na |
| 3-Cl-5-CF3-phenyl-O-C6H4-O-CH3 | H | CH3 | Na |
| 4-CF3-C6H4-O-C6H4-O-CH3 | H | CH3 | CH3 |

$$\underset{R}{R^1}N-C(=N-)N\underset{R^3}{R^2}$$ with X on central C

| R | R¹ | X | R² | R³ |
|---|---|---|---|---|
| H | tert. C4H9 | SCH3 | H | C2H5 |
| H | C2H5 | SCH3 | H | C2H5 |
| H | iC3H7 | SCH3 | H | C2H5 |
| H | CH3 | SCH3 | H | iC3H7 |
| H | iC3H7 | Cl | H | C2H5 |
| H | iC3H7 | Cl | H | cyclopropyl |
| H | C2H5 | Cl | H | C2H5 |
| H | C2H5 | Cl | H | -C(CH3)2CN |
| H | iC3H7 | Cl | H | iC3H7 |
| H | iC3H7 | OCH3 | H | iC3H7 |
| H | -C(CH3)2CN | OCH3 | H | cyclopropyl |
| H | C2H5 | Cl | H | -CH(CH3)CH2OCH3 |
| H | C2H5 | Cl | H | -CH(CH3)C≡CH |

$$\underset{R}{R^1}N-C(=O)-R^2$$

| R | R¹ | R² |
|---|---|---|
| CH3 | CH3 | CH(C6H5)2 |
| 1-naphthyl | H | 2-COOH-C6H4 |
| 3,4-dichlorophenyl | H | cyclopropyl |
| 3,4-dichlorophenyl | H | C2H5 |
| 5-chloro-4-methyl-2-thiazolyl | H | C2H5 |

| Structure | R¹/group | R² |
|---|---|---|
| 4-Cl-C6H4-CH3 | H | -C(CH3)2CH2CH2CH3 |
| 2-Cl-C6H4-CH2Cl | -CH(CH3)C≡CH | |
| 2-C2H5,6-CH2CH3-C6H3-CH2CH3 | -CH(CH3)CH2OCH3 | |
| 2,6-(C2H5)2-C6H3-CH2CC2H5 | -CH2OCH3 | |
| 2,6-(C2H5)2-C6H3-CH2CC2H5 | -CH2C(=O)OC2H5 | |
| 2-Cl-C6H4-CH2Cl | iC3H7 | |
| 2-CH3,6-CH2CH3-C6H3-CH2CH3 | -CH2-O-CH2-CH(CH3)2 | |

$$\underset{R}{R^1}N-C(=O)-R^2$$

| R | R¹ | R² |
|---|---|---|
| 2,6-(C2H5)2-C6H3 | -CH2-O-C4H9n | CH2Cl |
| 2,6-(CH3)2-C6H3-C2H5 | -CH2-O-C2H5 | CH2Cl |
| 2,6-(CH3)2-C6H3 | -CH2-(1,3-dioxolan-2-yl) | CH2Cl |
| 2,6-(CH3)2-C6H3 | -CH2-CH2-OCH3 | CH2Cl |
| 2-CH3,6-C2H5-C6H3 | -CH2-(4-methylpyrazol-1-yl) | CH2Cl |
| 2-CH3,6-C2H5-C6H3 | -CH2-(4-methoxypyrazol-1-yl) | CH2Cl |

-continued

| R | R¹ | R² |
|---|----|----|
| 2,6-dimethylphenyl | -CH₂-(1,2,4-triazol-1-yl) | CH₂Cl |
| 2,6-dimethylphenyl | -CH₂-(3,5-dimethylpyrazol-1-yl) | CH₂Cl |
| CH₃ | CH₃ | 1-ethyl-3,4,5-tribromopyrazol-yl |
| C₂H₅ | C₂H₅ | -CH(CH₃)-O-(1-naphthyl) |
| CH₂=CH-CH₂ | CH₂=CH-CH₂ | CH₂Cl |

Structure: R-N(R¹)-C(=O)-R²

| R | R¹ | R² |
|---|----|----|
| CH≡C-C(CH₃)₂- | H | 3,5-dichlorophenyl |
| 2-methyl-5-methyl-6-(F₃CSO₂NH)-phenyl | H | CH₃ |
| 2,4-dimethyl-6-(F₃CSO₂NH)-phenyl | H | CH₃ |

Structure: 4-NC-C₆H₂(X)(Y)-O-R

| X | Y | R |
|---|---|---|
| Br | Br | H (salts) |
| I | I | H (salts) |
| Br | Br | -C(=O)-(CH₂)₆-CH₃ |

2,4-dinitrophenyl-O-N=CH-(3,5-dibromo-4-hydroxyphenyl), salts, esters

2-CN-4-nitrophenyl-O-N=CH-(3,5-dibromo-4-hydroxyphenyl), salts, esters

Structure: R(R¹)N-C(=O)-N(R²)(R³)

| R | R¹ | R² | R³ |
|---|----|----|----|
| 4-isopropylphenyl | H | CH₃ | CH₃ |
| 2-chloro-4-methoxyphenyl | H | CH₃ | CH₃ |
| 3-(tert-C₄H₉NH-C(=O))-phenyl | H | CH₃ | CH₃ |
| benzothiazol-2-yl | H | CH₃ | H |
| benzothiazol-2-yl | CH₃ | CH₃ | H |
| 4-(4-chlorophenoxy)phenyl | H | CH₃ | CH₃ |
| phenyl | H | 2-methylcyclohexyl | H |
| 3-trifluoromethylphenyl | H | CH₃ | CH₃ |
| 4-chlorophenyl | H | CH₃ | -CH(CH₃)-C≡CH |
| 4-bromophenyl | H | CH₃ | OCH₃ |
| 3-methyl-4-chlorophenyl | H | CH₃ | CH₃ |
| 4-methylphenyl | H | CH₃ | -C(CH₃)₂-phenyl, H |

Structure: R(R¹)N-C(=O)-N(R²)(R³)

| R | R¹ | R² | R³ |
|---|----|----|----|
| 4-chlorophenyl | H | CH₃ | OCH₃ |
| 2-chloro-4-(ClCF₂S)-phenyl | H | CH₃ | CH₃ |
| 3,4-dichlorophenyl | H | CH₃ | CH₃ |
| phenyl | H | CH₃ | CH₃ |
| 4-chlorophenyl | H | CH₃ | CH₃ |

| Structure | R | R¹ | R² | R³ |
|---|---|---|---|---|
| cycloheptyl- | | H | CH₃ | CH₃ |
| 3,4-dichlorophenyl- | | H | CH₃ | OCH₃ |
| 3-bromo-4-chlorophenyl- | | H | CH₃ | OCH₃ |
| 3,4-dichlorophenyl- | | H | CH₃ | H |
| tert.H₉C₄-thiadiazolyl | | CH₃ | CH₃ | H |
| F₃C-thiadiazolyl | | CH₃ | CH₃ | H |
| 3,4-dichlorophenyl- | | H | C₂H₅ | C₂H₅ |
| F₂CHCF₂O-phenyl- | | H | CH₃ | CH₃ |
| H₃CO, Cl-phenyl- | | H | CH₃ | OCH₃ |
| Cl, H₃CO, Cl-phenyl- | | H | CH₃ | CH₃ |

Imidazolidinone-C(O)-NH-CH₂-CH(CH₃)₂ structure

Diphenyl ether structure with R¹, R², R³, R substituents:

| R | R¹ | R² | R³ |
|---|---|---|---|
| Cl | Cl | Cl | H |
| F | Cl | Cl | H |
| NO₂ | CF₃ | H | H |
| Cl | CF₃ | H | COOH (salts) |
| Cl | Cl | H | H |
| Cl | Cl | H | OCH₃ |
| Cl | Cl | H | —C(O)—OCH₃ |
| H | CF₃ | Cl | H |
| H | CF₃ | Cl | OC₂H₅ |

Triazinone structure with R, R¹, R²:

| R | R¹ | R² |
|---|---|---|
| tert. C₄H₉ | NH₂ | SCH₃ |
| tert. C₄H₉ | —N=CH—CH(CH₃)(CH₃) | SCH₃ |
| phenyl- | NH₂ | CH₃ |

Uracil-type structure with R, R¹, R², R³:

| R | R¹ | R² | R³ |
|---|---|---|---|
| H | CH₃ | Br | —CH(CH₃)—C₂H₅ |
| H | CH₃ | Br | iC₃H₇ |
| H | CH₃ | Cl | tert. C₄H₉ |
| H | CH₃ | Cl | tetrahydropyranyl |

Cyclopentane-fused uracil with cyclohexyl N-substituent

Nitrophenyl ether structure with R, R¹, R², R³:

| R | R¹ | R² | R³ |
|---|---|---|---|
| —C(O)—CH₃ | sec. C₄H₉ | H | H |
| H | CH₃ | H | H (salts, esters) |
| H | sec. C₄H₉ | H | H (salts, esters) |
| —C(O)—CH₃ | tert. C₄H₉ | H | H |
| —C(O)—CH₃ | tert. C₄H₉ | H | CH₃ |
| H | iC₃H₇ | CH₃ | H (salts, esters) |
| H | tert. C₄H₉ | H | H (salts) |

Oxadiazinone structure with X, Y, R:

| X | Y | R |
|---|---|---|
| CF₃ | H | CH₃ |
| H | F | CH₃ |

Benzoxazinone with phenyl substituent

-continued
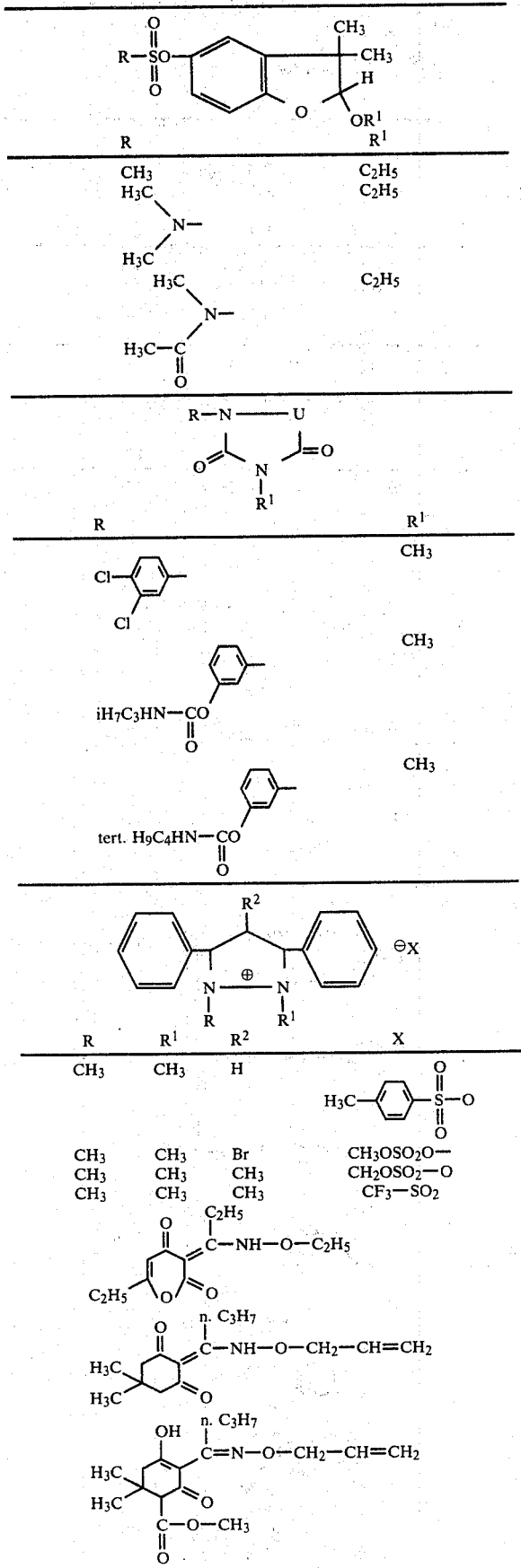
-continued
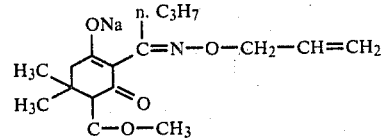
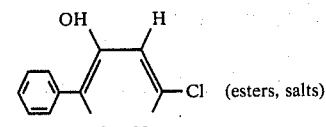
| R | R¹ | R² | R³ | R⁴ |
|---|----|----|----|----|
| Cl | Cl | NH₂ | Cl | COOH salts, esters |
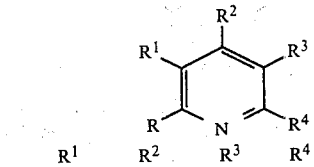
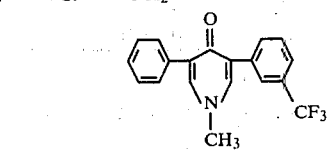
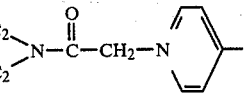
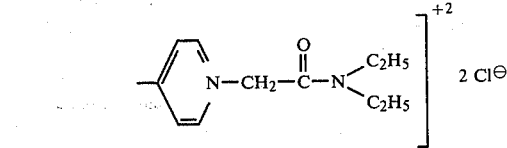
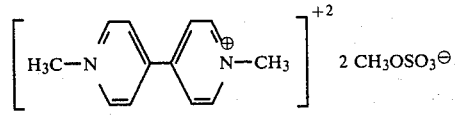
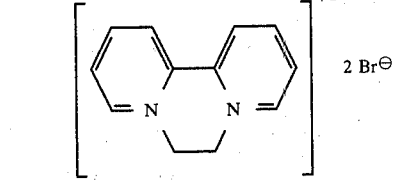
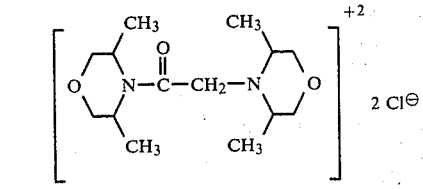
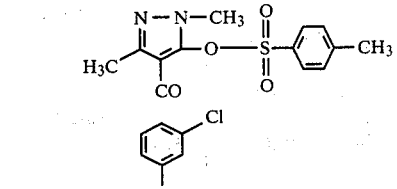

-continued

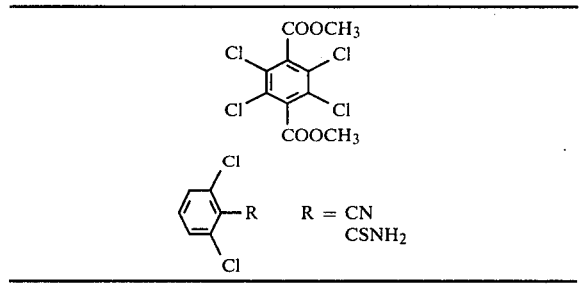

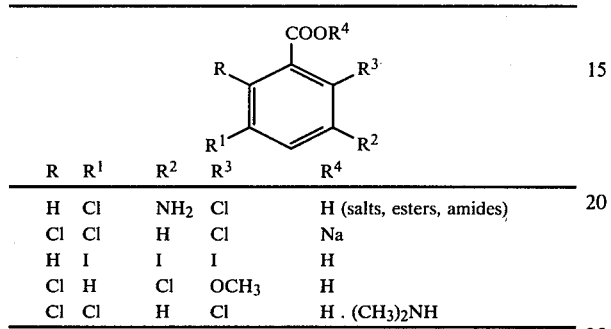

| R | R¹ | R² | R³ | R⁴ |
|---|----|----|----|-----|
| H | Cl | NH₂ | Cl | H (salts, esters, amides) |
| Cl | Cl | H | Cl | Na |
| H | I | I | I | H |
| Cl | H | Cl | OCH₃ | H |
| Cl | Cl | H | Cl | H . (CH₃)₂NH |

$$R-O-CH(R^1)-C(=O)-O-R^2$$

| R | R¹ | R² |
|---|----|----|
| 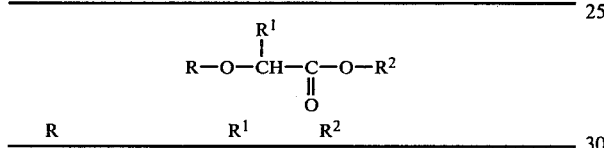 | CH₃ | H salts, esters, amides |
| 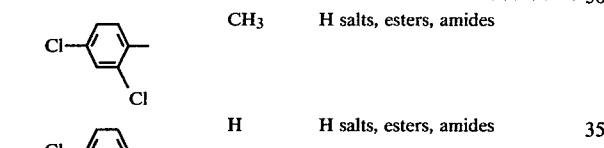 | H | H salts, esters, amides |
| 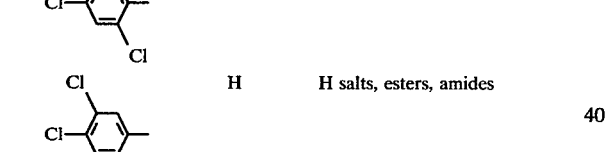 | H | H salts, esters, amides |
| 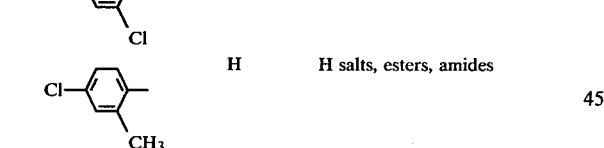 | H | H salts, esters, amides |
| 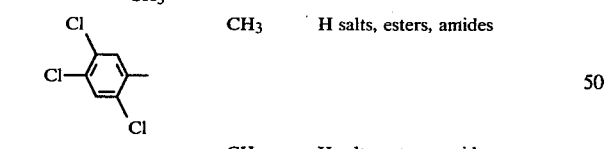 | CH₃ | H salts, esters, amides |
| 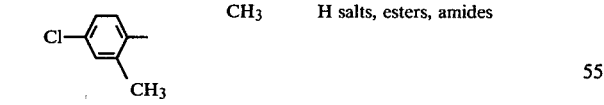 | CH₃ | H salts, esters, amides |

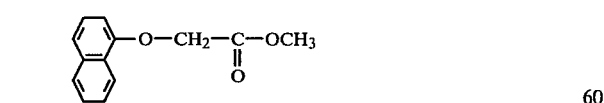

salts, esters, amides

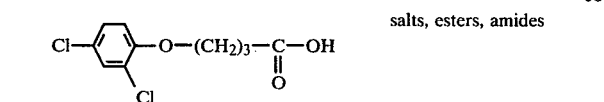

salts, esters, amides

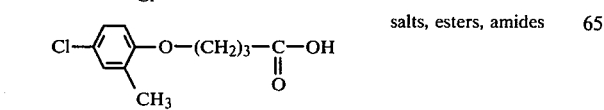

-continued

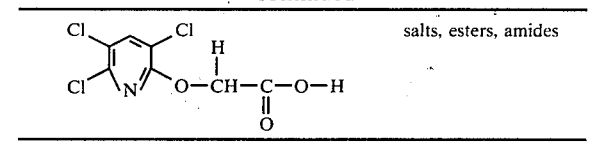 salts, esters, amides

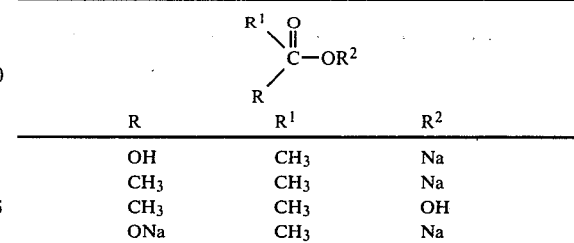

| R | R¹ | R² |
|---|----|----|
| OH | CH₃ | Na |
| CH₃ | CH₃ | Na |
| CH₃ | CH₃ | OH |
| ONa | CH₃ | Na |

$$R-N(R^1)-C(=O)-CH_2-O-S(=O)_2-R^2$$

| R | R¹ | R² |
|---|----|----|
| 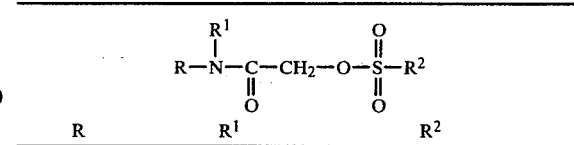 (2,3-dimethylphenyl) | CH₂—O—C₂H₅ | CH₃ |
| 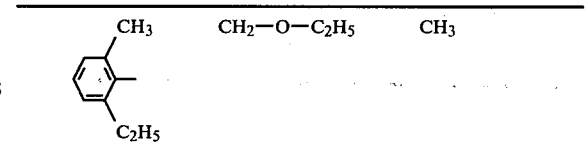 (2,3-dimethylphenyl) | CH₂—O—C₃H₇i | CH₃ |
| 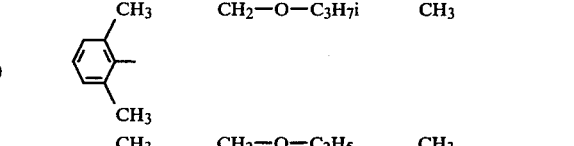 (2,3-dimethylphenyl) | CH₂—O—C₂H₅ | CH₃ |
| 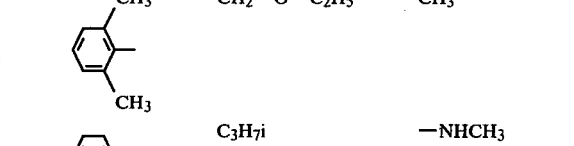 (phenyl) | C₃H₇i | —NHCH₃ |

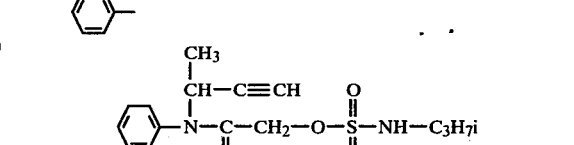

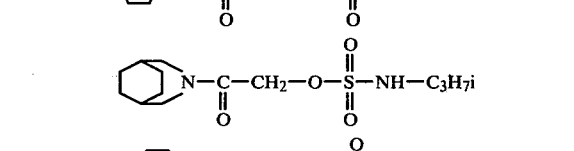

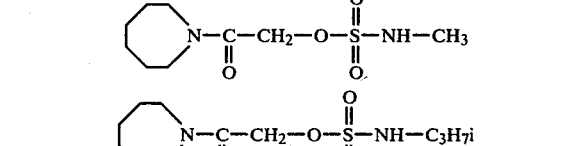

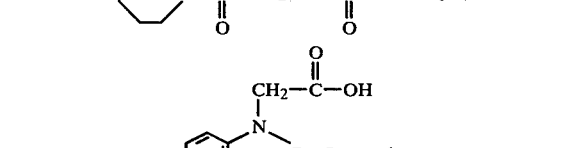

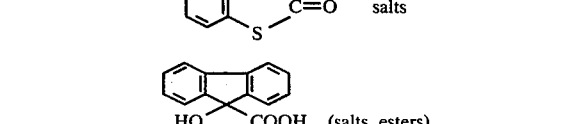 salts

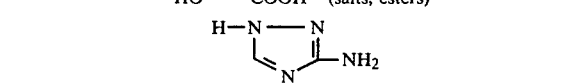 (salts, esters)

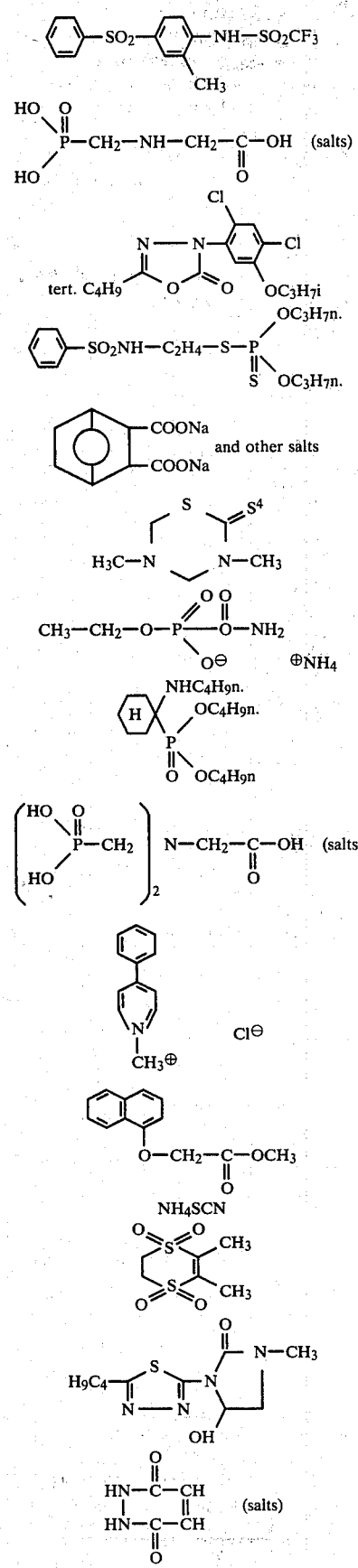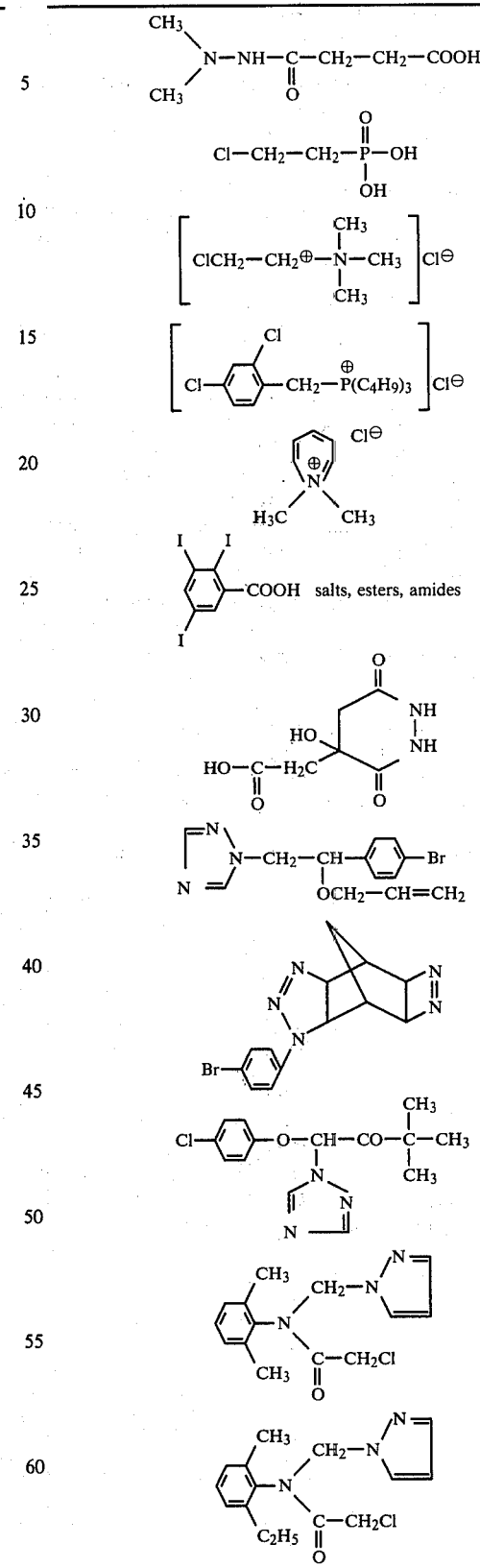
It may also be use to apply the new compounds, either alone or in combination with other herbicides, in admixture with other crop protection agents, e.g., agents for combating pests or phytopathogenic fungi or bacteria. The compounds may also be mixed with solutions of mineral matters used to remedy nutritional or trace element deficiencies.

Wetting agents, spreader stickers and non-phytotoxic oils may be added to initiate the herbicidal action.

The influence of various representatives of the compounds according to the invention on the growth of unwanted and crop plants in comparison with chemically similar, prior art compounds is demonstrated in the following experiments. The series of experiments were run in the greenhouse and in the open.

Working examples

Greenhouse experiments

The vessels employed were plastic flowerpots having a volume of 300 cm$^3$, and which were filled with a sandy loam containing about 1.5% humus. The seeds of the test plants (cf. Table 1) were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. After the agents had been applied, the vessels were lightly sprinkler-irrigated to induce germination and growth and to activate the chemical agents. Transparent plastic covers were then placed on the vessels until the plants had taken root. The cover ensured uniform germination of the plants, insofar as this was not impaired by the chemicals.

The pots were set up in the greenhouse-species from warmer areas at from 25° to 40° C., and species from moderate climates at 15° to 30° C. The experiments were run for from 4 to 6 weeks. During this period, the plants were tended and their reactions to the various treatments assessed. The following tables contain the compounds investigated, the application rates in kg/ha of active ingredient, and the plants used for the tests. The scale used for assessment was 0 to 100, 0 denoting no damage or normal emergence, and 100 denoting nonemergence or complete destruction of at least the visible plant parts.

Experiments in the open

The experiments were carried out on small plots with loamy and (pH 6), the humus content being from 1 to 1.5%. In the preemergence treatment, the compounds were applied either immediately after the crop plants had been sown or up to 3 days thereafter. The crop plants were sown in rows. The weed flora was natural. The substances were emulsified or dispersed in water as vehicle, and applied by means of a motor-driven plot spray mounted on a hitch. Where no rain fell, artificial irrigation was carried out to ensure germination and growth of the crop plants and weeds. All the experiments were run for several months. During this period, assessments on the 0 to 100 scale were made at certain intervals.

Results

The selective herbicidal action of the compounds according to the invention in both pre- and postemergence treatment will be apparent from the following tables.

TABLE 1

List of plant names

| Botanical name | Abbreviation in tables | Common name |
| --- | --- | --- |
| Alopecurus myosuroides | Alopec. myos. | slender foxtail |
| Amaranthus retroflexus | Amar. retr. | pigweed |
| Avena fatua | — | wild oats |
| Beta vulgaris | Beta vulg. | sugarbeet |
| Brassica napus | — | rape |
| Chenopodium album | Chenop. album | lambsquarters |
| Cyperus esculentus | Cyperus esc. | yellow nutsedge |
| Echinochloa crus galli | Echin. c.g. | barnyardgrass |
| Galinsoga spp. | Galin. spp. | — |
| Gassypium hirsutum | Gossyp. hirs. | cotton |
| Lamium spp. | — | dead-nettle |
| Setaria spp. | — | foxtail spp. |
| Solanum nigrum | Solan. nigrum | black nightshade |
| Stellaria media | Stell. med. | chickweed |
| Zea mays | — | Indian corn |

TABLE 2

Selective herbicidal action of the new acetanilides; preemergence treatment in the greenhouse

| Compound no. | kg/ha | Test plants and % damage |||||||
| --- | --- | --- | --- | --- | --- | --- | --- | --- |
| | | Brassica napus | Alopec. myos. | Avena fatua | Amar. retr. | Echin. c.g. | Setaria spp. | Solan. nigrum |
| 4 | 2.0 | 10 | 80 | 80 | 95 | 80 | 95 | 90 |
| 12 | 2.0 | 0 | 100 | 95 | 90 | 95 | 98 | 100 |
| 13 | 2.0 | 20 | 100 | 95 | 100 | 98 | 80 | 100 |
| 1 | 0.25 | 0 | 98 | 82 | — | 98 | 100 | 100 |

TABLE 3

Control of unwanted plants on postemergence treatment in the greenhouse

| Compound No. | kg/ha | Test plants and % damage ||||||
| --- | --- | --- | --- | --- | --- | --- | --- |
| | | Beta vulg. | Gossyp. hirs. | Alopec. myos. | Avena fatua | Cyperus esc. | Setaria spp. |
| 4 | 2.0 | 0 | 0 | 80 | 90 | 50 | 85 |
| 12 | 2.0 | 0 | 0 | 80 | 80 | 45 | 85 |
| 2 | 1.0 | 20 | 10 | 95 | 90 | 55 | 78 |

TABLE 4

Selective control of weeds in Indian corn by the new acetanilides; preemergence treatment in the open

| Compound no. | kg/ha | Test plants and % damage ||||||
| --- | --- | --- | --- | --- | --- | --- | --- |
| | | Zea mays | Echin. c.g. | Chenop. album | Galin. spp. | Stell. med. | Lamium spp. |
| 2 | 1.0 | 3 | 98 | 85 | 100 | 100 | 97 |

TABLE 4-continued

Selective control of weeds in Indian corn by the new acetanilides; preemergence treatment in the open

| Compound no. | kg/ha | Zea mays | Echin. c.g. | Chenop. album | Galin. spp. | Stell. med. | Lamium spp. |
|---|---|---|---|---|---|---|---|
| [structure: 2-C$_2$H$_5$, 6-CH$_3$ phenyl, N(CH(CH$_3$)CH$_2$OCH$_3$)(COCH$_2$Cl)] (prior art) | 1.0 | 0 | 99 | 42 | 70 | 53 | 67 |
| [structure: 2,6-di-C$_2$H$_5$ phenyl, N(CH$_2$OCH$_3$)(COCH$_2$Cl)] (prior art) | 1.0 | 0 | 94 | 51 | 90 | 47 | 60 |

EXAMPLE 2

90 parts by weight of compound 1 is mixed with 10 parts by weight of N-methyl-α-pyrrolidone. A mixture is obtained which is suitable for application in the form of very fine drops.

EXAMPLE 3

20 parts by weight of compound 2 is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

EXAMPLE 4

20 parts by weight of compound 3 is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

EXAMPLE 5

20 parts by weight of compound 1 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

EXAMPLE 6

20 parts by weight of compound 2 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

EXAMPLE 7

3 parts by weight of compound 3 is intimately mixed with 97 parts by weight of particulate kaolin. A dust is obtained containing 3% by weight of the active ingredient.

EXAMPLE 8

30 parts by weight of compound 4 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE 9

40 parts by weight of compound 1 is intimately mixed with 10 parts of the sodium salt of a phenolsulfonic acid-urea-formaldehyde condensate, 2 parts of silica gel and 48 parts of water to give a stable aqueous dispersion. Dilution in 100,000 parts by weight of water gives an aqueous dispersion containing 0.04 wt% of active ingredient.

EXAMPLE 10

20 parts of compound 2 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

We claim:

1. An acetanilide of the formula

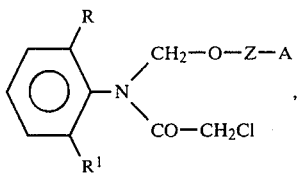

where R and R[1] are identical or different and each denotes alkyl of 1 to 4 carbon atoms, Z denotes methylene, or ethylene which is unsubstituted or substituted by 1 or 2 methyl groups, and A denotes pyrazole which is linked via a ring nitrogen atom and is unsubstituted or mono- or disubstituted by halogen, methyl or methoxy, triazole which is linked via a ring nitrogen atom and is unsubstituted or mono- or disubstituted by halogen, methyl or methoxy, or imidazole which is linked via a ring nitrogen atom and is unsubstituted or mono- or disubstituted by halogen, methyl or methoxy.

2. An acetanilide selected from the group consisting of 2-chloro-2',6'-dimethyl-N-(pyrazol-1-yl-methylenoxymethyl)-acetanilide and 2-chloro-2'-methyl-6'-ethyl-N-(pyrazol-1-yl-methylenoxymethyl)-acetanilide.

3. The acetanilide of claim 2 which is 2-chloro-2',6'-dimethyl-N-(pyrazol-1-yl-methylenoxymethyl)-acetanilide.

4. A herbicide containing a solid or liquid carrier and an effective amount of an acetanilide of the formula

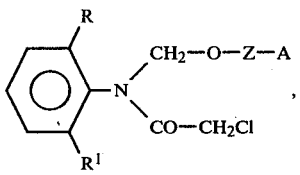

where R and R[1] are identical or different and each denotes alkyl of 1 to 4 carbon atoms, Z denotes methylene, or ethylene which is unsubstituted or substituted by 1 or 2 methyl groups, and A denotes pyrazole which is linked via a ring nitrogen atom and is unsubstituted or mono- or disubstituted by halogen, methyl or methoxy, triazole which is linked via a ring nitrogen atom and is unsubstituted or mono- or disubstituted by halogen, methyl or methoxy, or imidazole which is linked via a ring nitrogen atom and is unsubstituted or mono- or disubstituted by halogen, methyl or methoxy.

5. A herbicide comprising a liquid or solid carrier and a herbicidally effective amount of an acetanilide selected from the group consisting of 2-chloro-2',6'-dimethyl-N-(pyrazol-1-yl-methylenoxymethyl)-acetanilide and 2-chloro-2'-methyl-6'-ethyl-N-(pyrazol-1-yl-methylenoxymethyl)-acetanilide.

6. A process for controlling unwanted plant growth, which comprises treating the plants or the soil with a herbicidally effective amount of an acetanilide of the formula

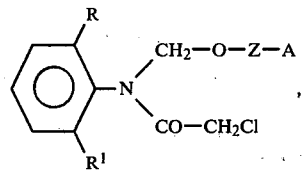

where R and R[1] are identical or different and each denotes alkyl of 1 to 4 carbon atoms, Z denotes methylene, or ethylene which is unsubstituted or substituted by 1 or 2 methyl groups, and A denotes pyrazole which is linked via a ring nitrogen atom and is unsubstituted or mono- or disubstituted by halogen, methyl or methoxy, triazole which is linked via a ring nitrogen atom and is unsubstituted or mono- or disubstituted by halogen, methyl or methoxy, or imidazole which is linked via a ring nitrogen atom and is unsubstituted or mono- or disubstituted by halogen, methyl or methoxy.

* * * * *